US009259541B2

(12) United States Patent
Temple

(10) Patent No.: US 9,259,541 B2
(45) Date of Patent: Feb. 16, 2016

(54) INSUFFLATION GAS HEATER SYSTEM AND TUBING FOR USE THEREWITH

(71) Applicant: John Temple, Chelsea, MI (US)

(72) Inventor: John Temple, Chelsea, MI (US)

(*) Notice: Subject to any disclaimer, the term of this patent is extended or adjusted under 35 U.S.C. 154(b) by 399 days.

(21) Appl. No.: 13/898,892

(22) Filed: May 21, 2013

(65) Prior Publication Data

US 2013/0274652 A1 Oct. 17, 2013

Related U.S. Application Data

(63) Continuation of application No. 12/902,826, filed on Oct. 12, 2010, now Pat. No. 8,444,591.

(60) Provisional application No. 61/250,144, filed on Oct. 9, 2009.

(51) Int. Cl.
*A61M 13/00* (2006.01)

(52) U.S. Cl.
CPC ............ *A61M 13/00* (2013.01); *A61M 13/003* (2013.01); *A61M 2202/0225* (2013.01); *A61M 2205/3331* (2013.01); *A61M 2205/3368* (2013.01); *A61M 2205/3653* (2013.01)

(58) Field of Classification Search
CPC .................. A61M 13/003; A61M 2205/3368; A61M 2205/3653; A61M 13/00; A61M 2202/0225; A61M 2205/3331; A61M 35/00; A61M 2202/0275; A61M 1/1698; A61M 1/1678; A61H 33/14; A61B 19/38; A61B 17/3474; A61F 11/00
USPC ..................................................... 604/23, 26
See application file for complete search history.

(56) References Cited

U.S. PATENT DOCUMENTS

| | | | | |
|---|---|---|---|---|
| 4,621,633 | A | * 11/1986 | Bowles | ............. A61M 16/1075 128/203.17 |
| 5,006,109 | A | 4/1991 | Douglas et al. | |
| 5,362,310 | A | * 11/1994 | Semm | ................. A61M 13/003 604/114 |
| 5,411,074 | A | 5/1995 | Naruse et al. | |
| 5,411,474 | A | * 5/1995 | Ott | ...................... A61M 13/003 600/560 |
| 5,439,441 | A | 8/1995 | Grimsley et al. | |
| 5,620,440 | A | * 4/1997 | Heckele | ................. A61B 18/00 392/384 |
| 6,010,118 | A | 1/2000 | Milewicz | |
| 6,068,609 | A | 5/2000 | Ott et al. | |
| 6,976,489 | B2 | 12/2005 | Mantell et al. | |
| 7,066,902 | B1 | 6/2006 | Ott et al. | |

(Continued)

FOREIGN PATENT DOCUMENTS

EP 0564953 A1 10/1993

*Primary Examiner* — Kami A Bosworth
*Assistant Examiner* — Bradley G Thomas, Jr.
(74) *Attorney, Agent, or Firm* — Dinsmore & Shohl LLP

(57) ABSTRACT

A warming gas flows through a jacket to heat an insufflation gas flowing in a separate tube, thereby reducing cost and disposable waste. The heated warming gas may be filtered to sterilize or maintain sterility and released to atmosphere after heating the flowing insufflation gas. Alternatively the warming gas may be reheated and recirculated through the jacket, with an additional tube being used within the jacket so that the warming gas flows in both directions lengthwise. As an alternative to separate tubes, a single, multi-lumen tube may be used. The insufflation gas may be $CO_2$ and the warming gas may be room air. The heating element and sensors may be separate from the disposable unit of a heated insufflation set, and need not be re-sterilized prior to or after use in surgery. The heat is constantly maintained, thereby eliminating "cold spots" caused by the natural cycling of the resistance heaters.

15 Claims, 6 Drawing Sheets

(56) References Cited

U.S. PATENT DOCUMENTS

| | | |
|---|---|---|
| 7,250,035 B1 | 7/2007 | Ott et al. |
| 7,429,257 B2 | 9/2008 | Novak et al. |
| 7,647,925 B2 | 1/2010 | Mantell et al. |
| 7,744,557 B2 | 6/2010 | Ott et al. |
| 2003/0014004 A1* | 1/2003 | Dey .................. A61M 13/003 604/26 |
| 2003/0181857 A1* | 9/2003 | Blake ................. A61B 17/3417 604/113 |
| 2004/0102731 A1 | 5/2004 | Blackhurst et al. |
| 2005/0171466 A1* | 8/2005 | Diemunsch ......... A61M 11/041 604/26 |
| 2006/0129098 A1 | 6/2006 | Hart et al. |
| 2006/0184096 A1 | 8/2006 | Ott et al. |
| 2007/0107726 A1 | 5/2007 | Mantell et al. |

* cited by examiner

Fig. 5A  Fig. 5B

INSUFFLATION GAS HEATER SYSTEM AND TUBING FOR USE THEREWITH

REFERENCE TO RELATED APPLICATIONS

This application is a continuation-in-part of U.S. patent application Ser. No. 12/902,826, filed Oct. 12, 2010, which claims priority from U.S. Provisional Patent Application Ser. No. 61/250,144, filed Oct. 9, 2009, the entire content of both of which is incorporated herein by reference.

FIELD OF THE INVENTION

This invention relates generally to instruments and methods used in minimally invasive surgery and, in particular, to apparatus and methods for heating insufflation gas of the type used in laparoscopic procedures.

BACKGROUND OF THE INVENTION

Laparoscopic surgery, also called minimally invasive surgery (MIS) is a recent development in which operations in the abdominal or pelvic cavities, for example, are performed through small incisions (usually 0.5-1.5 cm) as compared to larger incisions associated with "open" surgical procedures. Laparoscopic procedures typically use images displayed on TV monitors for magnification of the surgical elements as oppose to direct visualization by the surgeon.

There are a number of advantages to the patient with laparoscopic surgery versus an open procedure. These include reduced pain due to smaller incisions and hemorrhaging, and shorter recovery time. A key element is the use of a laparoscope, which may either be a telescopic rod lens system connected to a video camera or a digital laparoscope wherein an image sensor is located at the end of the laparoscope, thereby eliminating the rod lens system. Also attached is a fiber optic cable system connected to a light source (i.e., halogen or xenon), to illuminate the operative field.

During laparoscopic surgery, the abdomen (or other cavity) is usually insufflated, or blown up like a balloon, with carbon dioxide (or other) gas. This elevates the abdominal wall above the internal organs like a dome to create a working and viewing space. $CO_2$ is used because it is common to the human body and can be absorbed by tissue and removed by the respiratory system. It is also non-flammable, which is important because electrosurgical devices are commonly used in laparoscopic procedures.

It has been suggested that replacing cold, dry $CO_2$ with heated, humidified gas for insufflation during complex laparoscopic procedures offers certain benefits, including decreased hypothermia and peritoneal cell desiccation, with a resultant decrease in postoperative pain and a shortened recovery. This has led to the development of numerous heated insufflation sets, many of which include humidification apparatus.

One commercially available insufflation gas heater uses a separate heater "box" built into the set close to the patient. The heater is controlled by a separate heat controller remote from the heater, and may therefore be situated outside the sterile field. Other types use resistance wire heaters placed inside of the tubing. These wires are usually accompanied by an over-heat fuse. Some of these sets have wires which extend the overall length of the set, while others use resistance heating limited to the patient end. In some cases the wires are coiled; in other cases the wires are straight.

There are several drawbacks to these existing approaches. The deficiencies are related to the fact that the $CO_2$ gas does not flow continuously but is instead intermittent, with flow in the range of 0 to 40 liters per minute. When first filling the body cavity the flow is very high; a high flow rate may also occur at other points in the operation as the surgeon manipulates instruments. With the flow of cold $CO_2$, the controller delivers power to the resistance heater, and while this may occur rapidly, heat-up is limited by the need to avoid over heating which could burn the patient. Often times this results in unheated $CO_2$ entering the patient.

Also existing sets are very expensive, as the heating element in all of the sets is disposable. In products that use a heater "box," the entire heater unit either has to be autoclaved or thrown out and replaced with each use. The need remains for a more elegant solution.

SUMMARY OF THE INVENTION

This invention improves upon existing insufflation gas heaters through the use of a warming gas which flows through a jacket to heat an insufflation gas flowing in a separate tube, thereby reducing waste and the cost of the equipment involved. Since the $CO_2$ does not flow directly over a heater such as a resistance wire as it travels from an insufflator to a patient, the heating element (and sensors) may separate from the disposable unit of a heated insufflation set, thereby reducing disposable waste. The heating element and sensors also need not be cleaned or re-sterilized prior to, or after, use in surgery, which reduces the cost of production of the disposable set and or the operation. Moreover, the heat is constantly maintained, thereby eliminating "cold spots" caused by the natural cycling of the resistance heaters due to the nature of the operation being performed on the patient.

A basic system for heating insufflation gas in accordance with the invention comprises first and second tubes. The first tube carries insufflation gas from a proximal end to a distal end adapted for connection to an instrument used to inflate a body cavity with the insufflation gas. The second tube, surrounding or adjacent to the first tube, carries a warming gas to heat the first tube and the insufflation gas flowing therethrough. If the insufflation gas is already sufficiently warm, the system and method may be used to maintain temperature as opposed to "heating" it.

The system may include a filter for sterilizing the warming gas so that it may be released into a surgical field at the distal end after heating the first tube and insufflation gas. Alternatively, the system may include a third tube within the second tube for carrying the warming gas from the proximal end of the first tube to the distal end of the second tube where the warming gas is released to flow back toward the proximal end and around the first tube. A port at the proximal end enables the warming gas to exit the second tube so that it can be re-heated and recirculated back into the third tube.

As an alternative to separate tubes, multi-lumen tubes may be used in accordance with the invention. Such a tubing assembly would include a proximal end adapted for connection to a source of insufflation gas and a source of warming gas, and a distal end adapted for connection to an instrument used to inflate a body cavity with the insufflation gas. A flexible, elongated multi-lumen tube with an outer wall interconnects the proximal and distal ends of the tubing assembly. The multi-lumen tube includes a first lumen for flowing insufflation gas from the proximal end to the instrument, and at least one additional lumen for flowing a warming gas to heat or maintain the temperature of the insufflation gas as it flows through the first lumen.

BRIEF DESCRIPTION OF THE DRAWINGS

FIG. 5A is a cross section of a two-lumen tube constructed in accordance with the invention;

FIG. 5B is a cross section of a three-lumen tube;

DETAILED DESCRIPTION OF THE INVENTION

This invention relates to instruments and methods used in minimally invasive surgery (MIS) and, in particular, to apparatus and methods using a warming gas for heating insufflation gas of the type used in laparoscopic procedures. In all preferred embodiments, the insufflation gas is carbon dioxide and warming gas is air. Although any other non-flammable gas may be used for warming, certainly air is least expensive.

One embodiment of the invention uses two remote heaters; one to heat the $CO_2$ insufflation gas to body temperature prior to entering the patient, and a second heater to control a circular flow of warming gas (i.e., room air) in a jacketed tubing assembly to heat the insufflation gas. The heaters may both run at a constant temperature of approximately 98° F. (i.e., 98±7°). As such, heat entering the body will be approximately 98° because the $CO_2$ has been preheated and heat is not allowed to escape into the atmosphere through the tubing walls.

As an alternative to a separate heater for the insufflation gas, a single heater for the warming gas may be provided if the temperature and/or flow rate are sufficient. As a further alternative, a single heater may be used for the warming gas with the insufflation gas passing through a heat exchanger to pre-warm the insufflation gas prior to entry into the jacketed tubing assembly.

As described in further detail herein below, the jacketed tubing assembly may have one or two internal tubes, depending upon whether the warming gas is recirculated or released in to the environment. If the warming gas is recycled (and re-heated), it need not be sterile as it does not enter the sterile surgical field. If the warming air is released after use, it preferably passes through a filter to "sterilize" the air, (i.e., to remove bacteria or virus). This latter configuration has the advantage of requiring only two tubing layers. This approach is less costly, easier to manufacture, and the tubing set is lighter and more flexible which may be desired in the marketplace. A dispersing member may be used to diffuse the preheated gas as it exits the tubing.

Referring to the Figures, a system according to one embodiment of the invention includes a heater unit depicted generally at 10 and a tubing assembly shown generally at 100. The length of the tubing assembly is variable, but may be on the order of 10 feet, or thereabouts. It should be understood that these drawings are intended to illustrate important structural components and operational functionality and are not necessarily drawn to scale.

Figure 2:
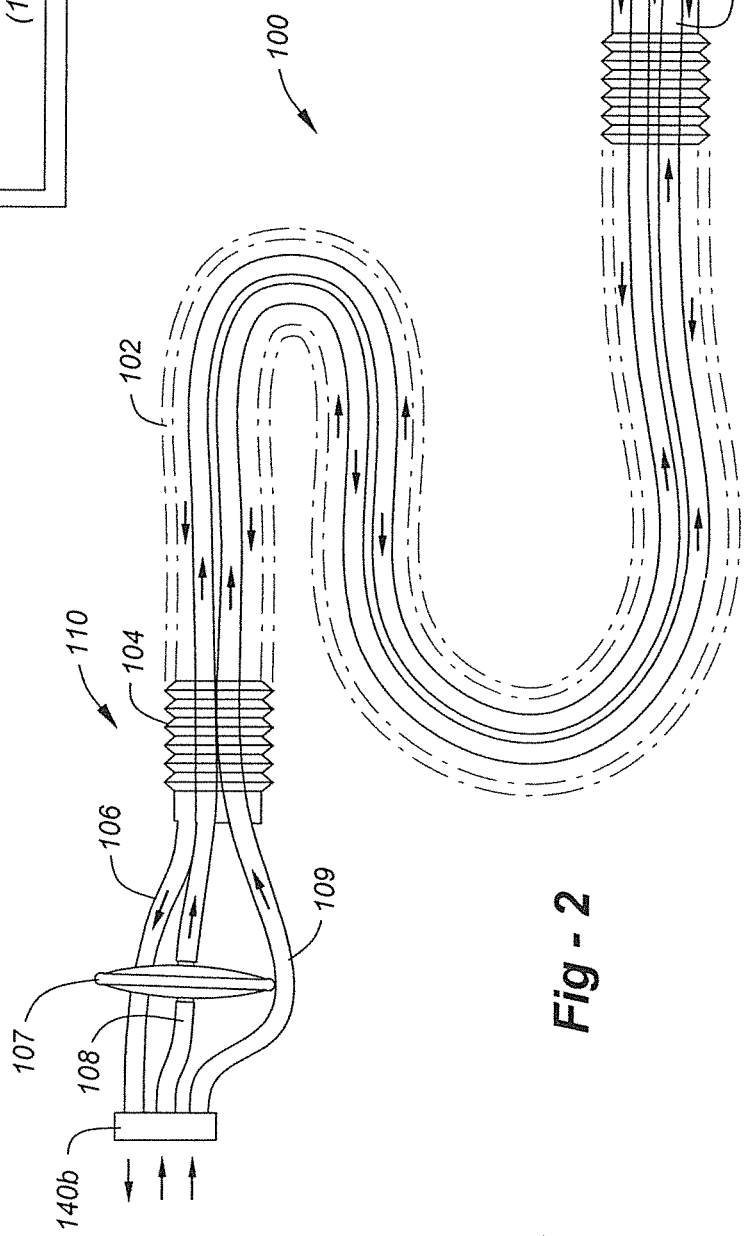
FIG. 2 depicts a tubing assembly for use with the heater of FIG. 1.

The tubing assembly 100 attaches to the heater unit 10 by way of a connector 140a, 140b as described in further detail with respect to FIG. 2. Insufflation gas such as carbon dioxide enters the heater unit 10 through port 14. The gas is carried by an appropriate conduit coupled to a source of pressure-controlled insufflation gas (not shown) at a rate typically in the range of 0.5-50 liters/min. or greater as technology allows. The insufflation gas passes through coupling 16 and into heater unit 18 which heats the gas. Heater unit 18 may be a Cast-X type heater from Watlow of St. Louis, Mo., a self-contained unit using medical grade stainless-steel tubing. Numerous alternative heating devices may be used. The heated insufflation gas passes through tube 20 and exits the heater via coupling 140a. All components are sterilized such that the sterility of the insufflation gas is maintained throughout.

Air or other warming gas is delivered by fan 24 and heated by heater 26 which may be a Model 375 finned strip heater, also available from Watlow. The warming gas is routed to tube 28 and through coupling 140a to the tubing assembly 100 at a flow rate in correlation to the heater temperature, which could be in the range of 1-2 cfm, enabling a desired heat to be maintained within the tube, depending upon the length of the tubing assembly and other factors. Return warming gas is received from inlet 22 through coupling 140a, which is recycled through fan 24 and reheated by heater 26 due to partition 12 in the heater unit 10.

Turning now to FIG. 2, as mentioned coupling 140b attaches to coupling 140a, thereby connecting tube 106 to tube 22; tube 108 to tube 20; and tube 109 to tube 28. Tube 108 carrying warmed $CO_2$ may pass through filter 107. The warming gas travels through tube 109 from the proximal end 110 of the assembly to the distal end 112, at which point it emerges into outer tube 102, which may include lengthwise accordion structure 104. As the warming gas travels back through the outer tube it heats or maintains the temperature of the $CO_2$ in tube 108, which may terminate in a standard Luer-Lok fitting 130 for interconnection to an instrument used for body cavity inflation.

In operation, the temperature of the gas used for insufflation may be maintained at a desired temperature, as in the range of 100° F. As such, the temperature of the warming gas may be set somewhat high to account for loss to the ambient environment. Although not shown, various temperature sensors and/or feedback systems may be incorporated to ensure reliable operation. For example, one or more thermistors may be included to monitor the temperature of either or both heaters or the gasses directly to maintain temperature control or to terminate heating if it becomes excessive.

All of the tubes depicted in FIG. 2 may be made of flexible plastic material. A distinct advantage of the system is that the tubing assembly 100 maintains temperature of the insufflation gas without the need for electrical heaters integral to the tubing, thereby reducing the cost of the tubing assembly 100, which is typically discarded and replaced following each procedure. Although separate tubes are shown for the insufflation gas and warming gas, in alternative embodiments an extrusion process may be used to form three or more tubes simultaneously so that they touch or are at least in close proximity.

Figure 1:
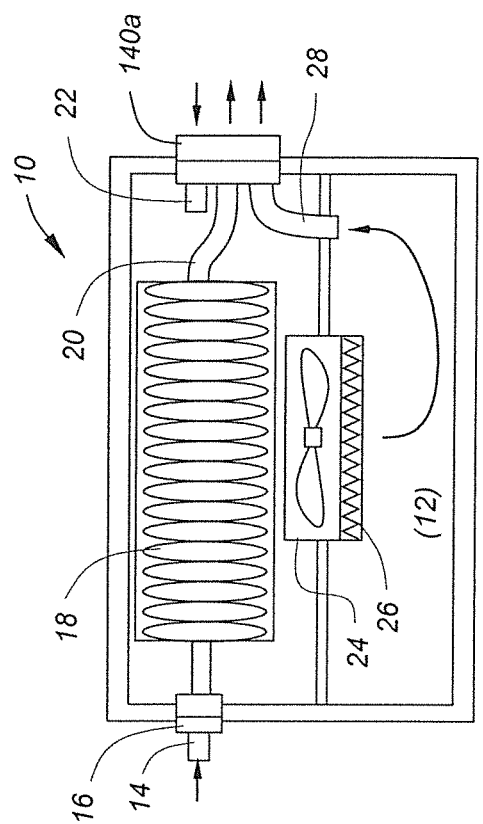
FIG. 1 is a schematic diagram of a device to heat insufflation gas constructed in accordance with the invention.

In the embodiment of FIGS. 1, 2 the warming gas is recycled and not released into the ambient atmosphere of the surgical suite. This has two advantages: one, the warming gas need not be sterile (through filtration may be added for such purpose), as the system is closed-loop; and two, the previously heated warming gas is essentially re-heated, which may cut down on power requirements. A disadvantage, however, is that the tubing assembly 100 required three passageways—one for the insufflation gas and two for the warming gas The embodiment of FIGS. 3, 4 uses an additional filter 411 to ensure that the warming gas is sterile, enabling the gas to be released through port 412 at the distal end 420 of the tubing assembly. Although the warming gas filter is shown at the proximal end of the tubing assembly, it may alternatively be positioned inside the heater unit 10 or at the distal end 420 immediately prior to the exit port 412.

Figure 3:
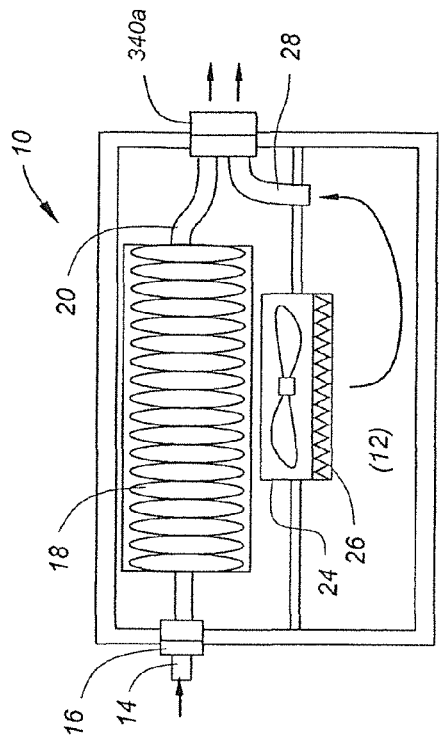
FIG. 3 depicts an alternative heater.
Figure 4:
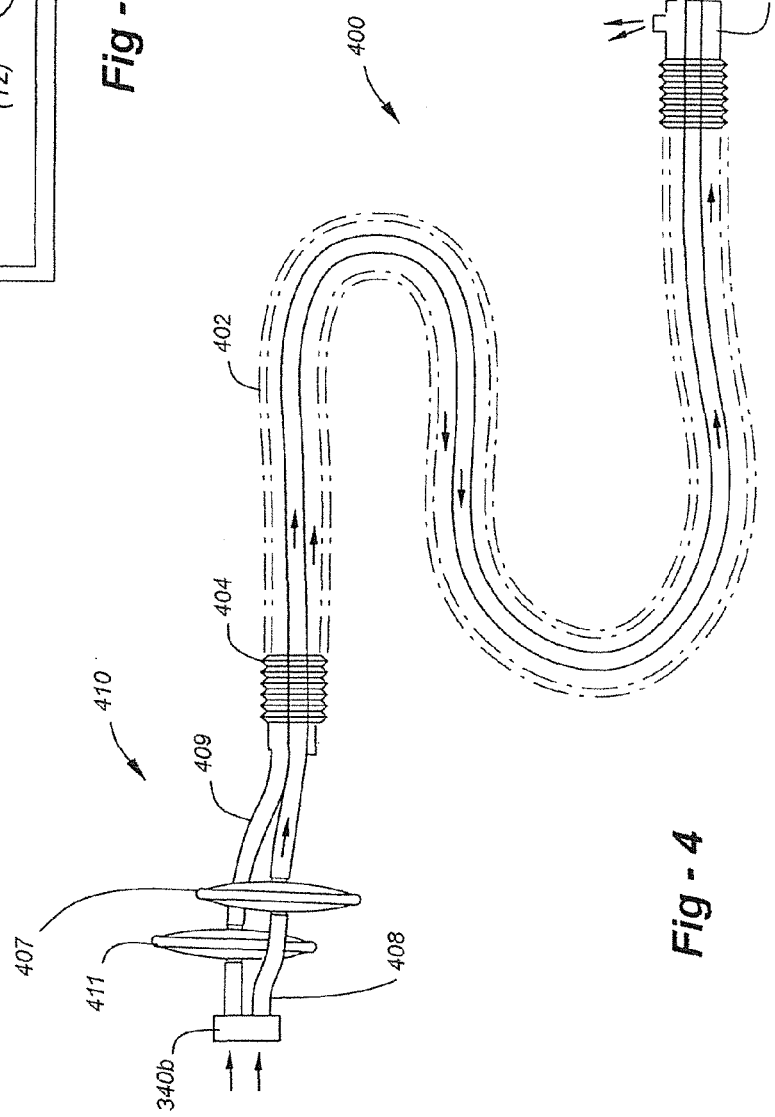
FIG. 4 is a drawing that shows an alternative tubing assembly which eliminates a return heated gas line.

Otherwise the system and method of FIGS. 3, 4 is similar to those described with reference to FIGS. 1, 2. The tubing assembly 400 connects to the heater unit 10 through connector 340a, which now only has two passageways. Connector 340a connects to 340b, coupled to hoses 408, 409, which are filtered by filters 407, 411, respectively. Tube 402, containing only one inner conduit 408 (which terminates at connector 430), may be smaller in diameter and less expensive. As with tube 102, tube 402 may include an accordion structure shown schematically at 404.

As discussed earlier, if the temperature and/or flow rate of the warming gas is sufficient, a separate heater for the insufflation gas (i.e., heater unit 18 in FIGS. 1 and 3) may be eliminated. As a further alternative, the insufflation gas may pass through a heat exchanger associated with heating the warming gas (i.e., heater 26 in FIGS. 1 and 3) prior to entry into the heater assemblies shown in FIGS. 2, 4. In all embodiments, the heater(s) may be located at any point(s) in the system, including as a separate box, integral to the insufflator, or within the tubing "set."

As an alternative to separate tubes, multi-lumen tubes may be used in accordance with the invention. Such tubes may be extruded from polyurethane or other suitable plastic or polymeric materials. FIG. 5A is a cross section of a two-lumen tube; FIG. 5B is a cross section of a three-lumen tube; and FIG. 5C is a cross section of a multi-lumen tube. In FIG. 5A, either lumen 502, 504 could be used for the insufflation gas or warming gas, with the warming gas being expelled at the distal end as there is no return warming gas path. In preferred configurations, the insufflation gas channel is larger in diameter and central to the tube as shown as 512 in FIG. 5B. This allows on or more heating gas channels 514, 516 to 'surround' the central channel 512, facilitating a return path(s) and recycling/reheating of the warming gas. FIG. 5C illustrates numerous warming gas channels 524 surrounding a central insufflation gas channel 522.

Figure 5E:
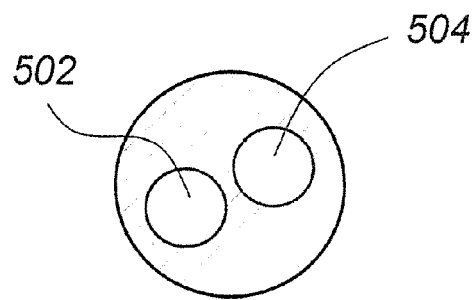
FIG. 5E is a cross section of a multi-lumen tube with saddle-shaped air channels.
Figure 5E:
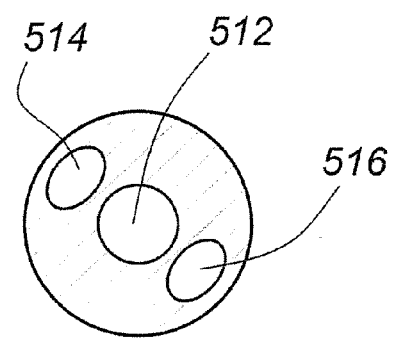
Figure 5E:
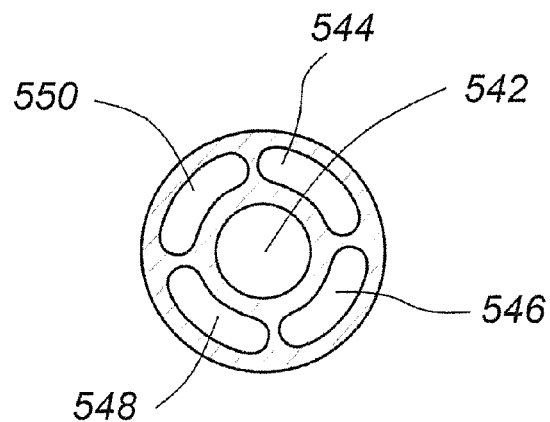
Figure 5C:
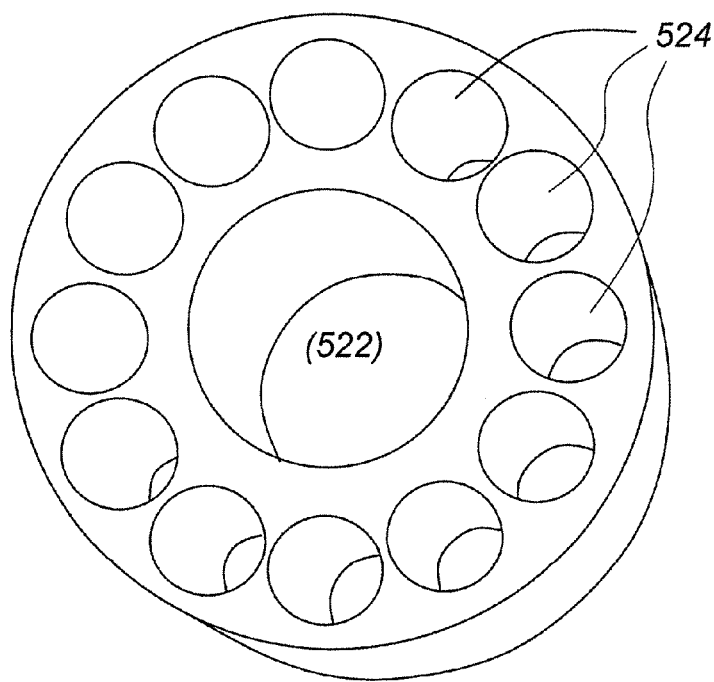
FIG. 5C is a cross section of a multi-lumen tube.
Figure 5D:
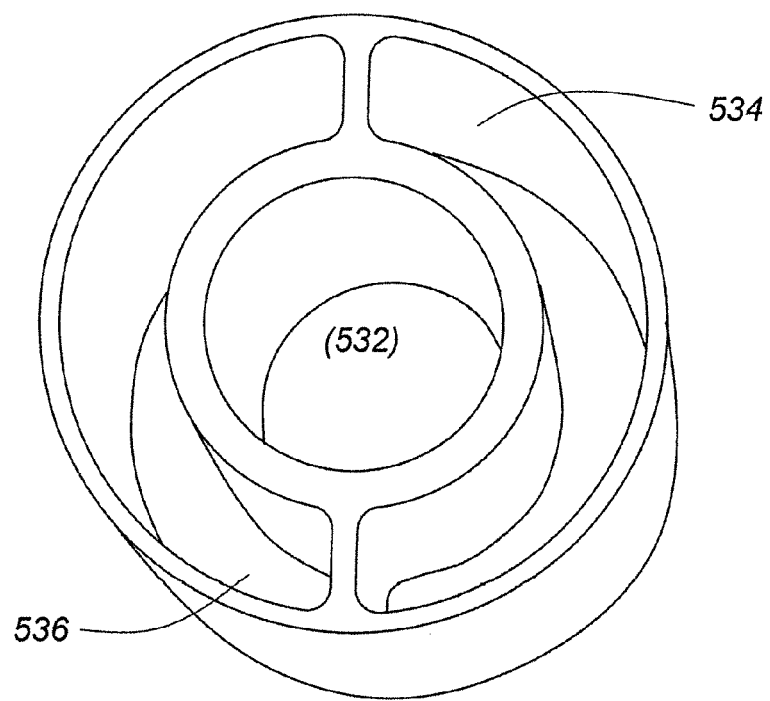
FIG. 5D is a cross section of a three lumen tube with saddle-shaped air channels.

To enhance the efficiency of heating and/or insulation, FIG. 5D is a cross section of a three lumen tube with saddle-shaped air channels, and FIG. 5E is a cross section of a multi-lumen tube with saddle-shaped air channels. In FIG. 5D, insufflation gas is carried by channel 532, with channels 534, 536 being used for warming gas, whether or not recirculated. If tube 'kinking' is an issue, ribs may be added to produce a greater number of saddle-shaped channels as shown in FIG. 5E. As with other embodiments, all of the channels 544, 546, 548, 550 may be used for 'outgoing' warming gas, or some may be used for recirculation. For example, gas through 544 may be brought back through 546, and gas through 548 may be brought back through 550. Once 'brought back,' the gas may be reheated or simply sent out a different lumen for further recirculation, depending upon temperature requirements.

Figure 6A:
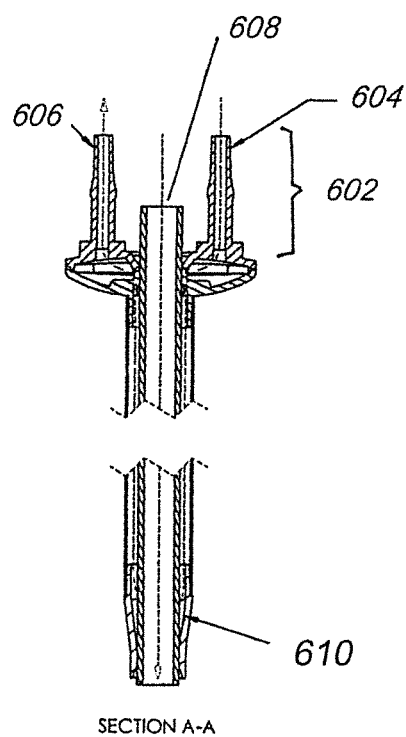
FIG. 6A is a cross section of a tubing assembly utilizing the tube of FIG. 5D.
Figure 6B:
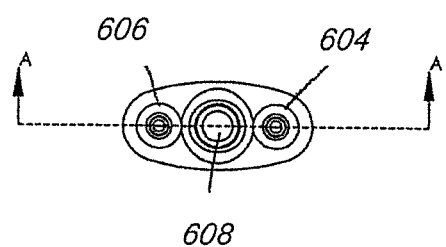
FIG. 6B is an end-on view of the assembly of FIG. 6A.

FIG. 6A is a cross section of a tubing assembly utilizing the tube of FIG. 5D, and FIG. 6B is an end-on view of the assembly of FIG. 6A. This assembly includes a proximal connector 602 that interfaces to the insufflator apparatus. The connector 602 includes a hot air input port 604 and a warm air return port 606. Insufflation gas is delivered through port 608. The assembly includes a distal end 610 providing an air turnaround structure such that hot air is carried out by one of the channels 534, 536 of FIG. 5D, with the recirculated air being returned to the insufflator through the other lumen.

In the embodiment just described, the $CO_2$ is preheated to body temperature. The warming air is room air heated to 104 or 105 degrees on the out flow, and returning at about 80 plus degrees. The outer luminal flow is not necessarily intended to heat the inner or center lumen $CO_2$ but only to maintain its temperature. Such heat may be maintained by the temperature and/or speed of the flow of the warming gas. The fan (i.e., 24) in the insufflator may be replaced with a pump to ensure flow speed and variable speed to maintain temperature of our circulating air.

I claim:

1. A system for heating or maintaining the temperature of an insufflation gas, comprising:
a tubing assembly having a proximal end adapted for connection to a source of insufflation gas and a source of warming gas, and a distal end adapted for connection to an instrument used to inflate a body cavity with the insufflation gas; and said tubing assembly including a flexible, elongated multi-lumen tube with an outer wall between the proximal and distal ends of the tubing assembly, the multi-lumen tube including: a first lumen for flowing insufflation gas from the proximal end to the instrument, and at least one additional lumen for flowing a warming gas to heat or maintain the temperature of the insufflation gas as it flows through the first lumen.

2. The system of claim 1, wherein the first lumen and the multi-lumen tube share a common longitudinal centerline.

3. The system of claim 1, wherein:
the first lumen is central to the multi-lumen tube; and
an additional lumen between the first lumen and the outer wall of the multi-lumen tube.

4. The system of claim 1, wherein:
the first lumen is central to the multi-lumen tube; and
a plurality of additional lumens between the first lumen and the outer wall of the multi-lumen tube.

5. The system of claim 1, wherein:
the first lumen is central to the multi-lumen tube;
a plurality of additional lumens between the first lumen and the outer wall of the multi-lumen tube; and
a redirection structure at the distal end of the tubing assembly enabling warming gas flowing from the proximal end to the distal end in one of the additional lumens to flow from the distal end and back to the proximal end in a different one of the additional lumens.

6. The system of claim 1, wherein:
the first lumen is central to the multi-lumen tube;
a plurality of additional lumens between the first lumen and the outer wall of the multi-lumen tube;
a redirection structure at the distal end of the tubing assembly enabling warming gas flowing from the proximal end to the distal end in one of the additional lumens to flow from the distal end and back to the proximal end in a different one of the additional lumens; and
a port at the proximal end enabling the warming gas to be re-heated and returned to the tubing assembly.

7. The system of claim 1, wherein the heated warming gas is released into the ambient environment at the distal end of the tubing assembly.

8. The system of claim 1, wherein:
the heated warming gas is released into the ambient environment at the distal end of the tubing assembly; and
a filter to filter the warming gas prior to being released.

9. The system of claim 1, wherein:
the first lumen is central to the multi-lumen tube; and the additional lumen forming a partial cylindrical channel surrounding at least a portion of the first lumen along the length of the multi-lumen tube.

10. The system of claim 1, wherein:
the first lumen is central to the multi-lumen tube; and
a plurality of additional lumens, each forming a partial cylindrical channel surrounding at least a portion of the first lumen along the length of the multi-lumen tube.

11. The system of claim 1, wherein:
the first lumen is central to the multi-lumen tube;
a plurality of additional lumens, each forming a partial cylindrical channel surrounding at least a portion of the first lumen along the length of the multi-lumen tube; and
a redirection structure at the distal end of the tubing assembly enabling warming gas flowing from the proximal end to the distal end in one of the additional lumens to flow from the distal end and back to the proximal end in a different one of the additional lumens.

12. The system of claim 1, further including a heater for heating the insufflation gas.

13. The system of claim 1, further including a heater for heating the warming gas.

14. The system of claim 1, wherein the insufflation gas is carbon dioxide.

15. The system of claim 1, wherein the warming gas is air.

* * * * *